Figure 1:
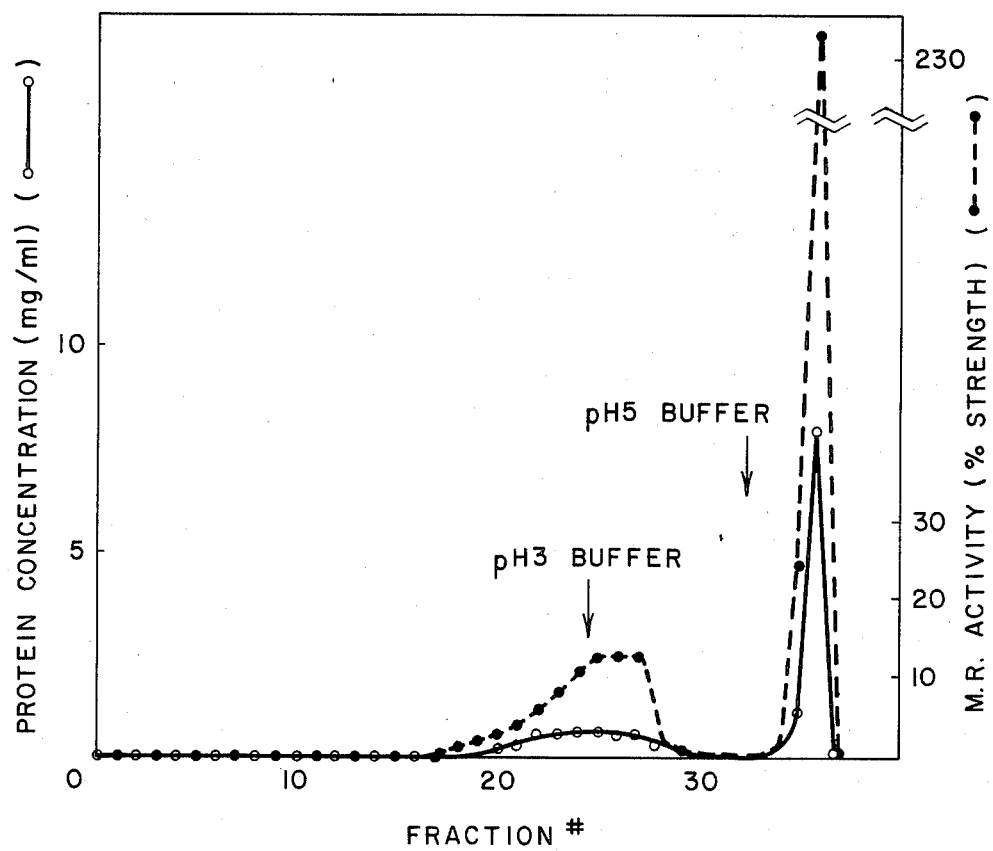

United States Patent [19]

Subramanian

[11] Patent Number: 4,743,551

[45] Date of Patent: May 10, 1988

[54] **PURIFICATION OF MICROBIAL RENNET FROM *MUCOR MIEHEI***

[75] Inventor: Sethuraman Subramanian, Elkhart, Ind.

[73] Assignee: Miles Inc., Elkhart, Ind.

[21] Appl. No.: 668,404

[22] Filed: Nov. 5, 1984

[51] Int. Cl.[4] .............................................. C12N 9/64
[52] U.S. Cl. ................................... 435/226; 435/219; 435/815
[58] Field of Search ................ 435/183, 68, 219, 223, 435/226, 815

[56] References Cited

U.S. PATENT DOCUMENTS 4,666,843  5/1987  Subramanian .

OTHER PUBLICATIONS

Kobayaski et al, *Analytical Biochemistry*, 122, 308–312 (1982).
Subramanian, CRC *Critical Reviews in Biochemistry*, vol. 16, (1982).
Issue 2, pp. 169–205, Dean et al, *J. Chromatogs*, 165, 301 (1979).
Burgett et al, *Am. Lab.*, p. 74 (1977).

*Primary Examiner*—Thomas G. Wiseman
*Assistant Examiner*—Stephanie Seidman
*Attorney, Agent, or Firm*—Jerome L. Jeffers

[57] ABSTRACT

A method for the purification of a culture filtrate resulting from the fermentation of an organism of the species *Mucor miehei* involves the selective adsorption of the microbial rennet present in the culture filtrate by a blue dye affinity ligand with subsequent elution of the adsorbed microbial rennet to provide it in a purified form.

10 Claims, 1 Drawing Sheet

PURIFICATION OF MICROBIAL RENNET FROM *MUCOR MIEHEI*

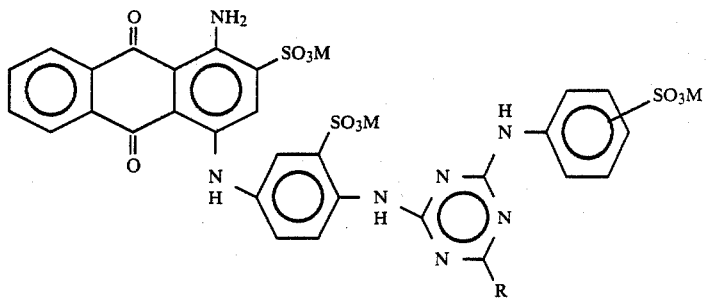

BACKGROUND OF THE INVENTION

Traditionally, calf rennet has been used as a milk coagulant in the production of cheese. In recent years, dramatic increases in worldwide cheese production and decreases in calf rennet supplies have stimulated the use of alternative milk coagulating enzymes. Among the available enzymes suitable for this purpose, the microbial rennets are favored because they can be mass produced and offer a variety of properties permitting selection of those most suitable for cheese production. A microbial rennet which has achieved significant commercial success is obtained during the fermentation of an organism from the species *Mucor miehei*. In the traditional method of preparing microbial rennet from this organism, the fermentation is carried out in a suitable nutrient medium and purification is carried out by filtering the fermentation broth, adjusting the pH of the filtrate, concentrating the filtrate and then using ultrafiltration and vacuum evaporation techniques to complete the purification. While this method is reasonably effective, carbohydrates, pigments and extraneous enzymes tend to accumulate in the final product. Furthermore, the targeted recovery of 85% enzyme activity is not always achieved.

Kobayashi, et al report in *Analytical Biochemistry*, 122, 308-312 (1982) that microbial rennet from *M. miehei* and *Endothia parasitica* was purified by the use of affinity columns including N-acetylpepstatin affinity gel.

Subramanian reports in *CRC Critical Reviews in Biochemistry*, Vol. 16, Issue 2, pages 169-205 (1984) that Cibacron Blue F3GA(CB) has ascended in status from a lowly textile dye to a glorified "biospecific" ligand in less than a decade.

Dean, et al in *J. Chromatogr.*, 165, 301 (1979) and Burgett, et al in *Am. Lab.*, p. 74 (1977) enumerate a large number of enzymes which have successfully been separated on a CB column. These enzymes include hexokinase, DNA-polymerase, alcohol dehydrogenase, adenylate kinase, ribonuclease, glyoxalase 1, cytochrome C, aldolase, blood clotting factor X and enolase. The enzymes do not have many features in common either in terms of structure or function.

SUMMARY OF THE INVENTION

The present invention is a method for purification of a culture filtrate derived from the fermentation of a microbial rennet producing strain of *Mucor miehei* which filtrate contains microbial rennet together with other protein impurities which method comprises:

(a) contacting the culture filtrate with an affinity ligand of the formula:

where M is a monovalent or divalent cation and R is a solubilizing moiety or a moiety which will insolubilize the ligand without affecting its affinity characteristics, at a pH below 4.0 to cause the selective adsorption of the microbial rennet to the ligand thereby forming a ligand/microbial rennet complex;

(b) separating the ligand/microbial rennet complex from the other protein impurities; and (c) recovering the microbial rennet from the ligand/microbial rennet complex.

DESCRIPTION OF THE INVENTION

The blue dye affinity ligand set out above is available commercially as Cibacron Blue F3GA in a form in which M is Na and R is Cl. This form of the dye is soluble and can be used to purify the microbial rennet. The dye, if it binds to an appropriate site on the enzyme, can neutralize three positive charges and thereby lower the iso-electric point of the enzyme in the enzyme-dye complex. In the case of *M. miehei* rennet, the enzyme precipitates when enough dye is added and the precipitate can be centrifuged, redissolved in salt and the redissolved dye removed by precipitation with polycations such as chitosan. The clear supernatant contains the enzyme in the pure state.

Other soluble forms of the dye, such as when R is polyethylene glycol, dextran or polyethyleneimine can be used in the purification of microbial rennet in a similar manner. When R is polyethylene glycol, two-phase purification can be used. Two-phase purification involves the use of Cibacron blue derivatized polyethyleneglycol (CB-PEG) and dextran in water to form two phases. The upper phase will be rich in CB-PEG and the lower phase rich in dextran. The enzyme (microbial rennet) will complex with CB-PEG and stay in the upper phase. When the upper phase is separated and treated with salt (NaCl) there will be further separation into two phases. The enzyme will be released into aqueous (containing salt) phase. When R=dextran, the enzyme forms a blue dextran-enzyme complex which can be separated on a gel filtration column. The enzyme can be dissociated from the complex with salt and rechromatographed to separate it from the blue dextran. With polyethyleneimine, the enzyme may form a precipitate or a complex which can be chromatographed further to separate the enzyme.

In a preferred method of practicing the present invention, the affinity ligand is immobilized by attaching it to a polymeric material so that in the foregoing formula R is agarose, Sephadex (dextran cross-linked with epichlorhydrin), polyacrylamide, agarose-polyacrylamide copolymer, cellulose, or glass among other insoluble matrices. A particularly preferred insoluble affinity ligand is available as Blue agarose in which M in the above formula is Na and R is cross-linked agarose. Blue agarose has good flow properties as well as good mechanical and chemical stability. It is highly porous and the gel is known to be stable for years. These bead-like particles lend themselves readily for use in a conventional affinity gel chromatography column.

In the above formula, M can represent a monovalent or divalent cation such as $Li^+$, $Na^+$, $K^+$, $Rb^+$, $Ca^{++}$ or $Mg^{++}$. Depending on the coordination number of the $SO_3^-$ groups of the dye complexed to the metal, there can be excess negative or positive charge on the dye-metal ion complex if the cation is divalent. Typically the cation is $Na^+$.

The culture filtrate obtained after the fermentation of *M. miehei* contains proteins other than the desired microbial rennet. These other proteins are, for example, α-amylase, glucoamylase, cellulase and lipase. The present invention resides in the discovery that the blue dye affinity ligand will, at a pH below 4.0, bind the microbial rennet protein in a selective manner when the two are contacted in the presence of the other proteins present in the culture filtrate. Typically, the gel column is washed with the loading buffer prior to the elution step. The washing step removes any physically trapped impurities from the culture filtrate that stay in the liquid volume of the column when the loading is completed. Instrumental in the usefulness of this process is the discovery that the bound microbial rennet can be eluted from the affinity ligand. Elution may be achieved by salt which is preferred in some cases for preservation of the enzyme. The buffer used for loading the enzyme, washing and elution is citrate buffer at a concentration of 0.05M. The pH of loading buffer is typically 3.0 and eluting buffer has a pH of 5.0. Peak MR activity is eluted at a pH of 4.2 and all MR activity is eluted at a pH $\leq 4.8$.

If salt is used to elute the bound enzyme, it can be used at pH 3.0 or at any pH between 3 and 5. The typical salt is NaCl although other salts can be used. At pH 3.0, peak MR activity is eluted at a NaCl concentration of 0.4M NaCl. Complete elution can be effected at a NaCl concentration of <1.0M. At pH 5.0, NaCl is not needed for elution. However, it can be present for purposes of preventing microbial growth during storage. The flow rates depend on the column width and height. Generally, flow rates can be varied in direct proportion to the width of a column. A flow rate of 67 ml/hr. in a column 1 cm×12 cm has been used without experiencing any difficulty. The enzyme, whether eluted at a pH of 5 or with NaCl, can be obtained at a high concentration.

The Blue dye affinity ligand has no effect on extraneous pigments normally present in the *Mucor miehei* culture filtrate. These pigments can be removed by a pre-purification step in which the filtrate is passed through a cation exchange column.

The present invention is further illustrated by the following example.

EXAMPLE I

A culture filtrate of microbial rennet from an organism of the species *Mucor miehei* was prepared using submerged fermentation of strain NRRL 3420 in an aqueous nutrient medium. At the end of the fermentation period, the drop was filtered to remove the biomass and the filtrate processed as follows:

The pH of this filtrate was adjusted to 3.0 from 6.1 by the addition of concentrated HCl and then passed through a precolumn containing Dowex AG-50W-X4 (polystyrene sulfonate) cation exchange resin containing sulfonic acid groups which removed pigments but did not bind the microbial rennet. The effluent of this precolumn was fed into a 1 cm diameter×15 cm high column containing beads of Blue agarose gel which comprises a support matrix of 4% beaded agarose with Cibacron F3GA as the attached ligand. The pellets had a wet bead diameter in the range of 40–190 μm (100–200 mesh). Enough culture filtrate was passed through the column to saturate its capacity whereupon the column was washed with 0.05M sodium citrate buffer at pH 3.0. Absorbance of the pass-through and elution fractions was measured with a UV spectrometer at 280 nm to detect the presence of microbial rennet. When the effluent showed negligible absorbance at 280 nm, a 0.05M sodium citrate solution was adjusted to pH 5.0 with concentrated NaOH and used to elute the bound microbial rennet. Most of the enzyme was eluted in one small fraction thereby purifying and concentrating the microbial rennet. The recovery was close to 85% as determined by measuring the total milk clotting activity in the quantity of microbial rennet loaded and that which was eluted from the column. FIG. 1 represents a chromatogram of culture filtrate of microbial rennet using polystyrene sulfonate and Blue gel in a tandem arrangement employed as described above. Each fraction represents a volume of 7.3 ml collected consecutively. The arrows in FIG. 1 represent the points at which the irrigating buffer and the elution buffer were applied. Table 1 provides the quantitative details with respect to the purification procedure. The enzyme strength in a typical elution is 233% while that of the culture filtrate is 10%. The protein concentration in the culture filtrate is 0.78 mg/ml and that of the eluted enzyme is 8 mg/ml. The concentration achieved in protein is 10.25 fold while enzyme is concentrated 23.5 fold. Thus, the specific activity has been increased from 12.7 (starting material) to 29 in the eluted product. This is an indication of removal of extraneous proteins. Lipase activity in the eluted product was negligible. The end product is practically colorless and almost free of carbohydrates.

TABLE 1

A. Characteristics of initial and final enzyme products

| | OD at 280 nm | OD at 450 nm | MR Strength % | Protein (mg/ml) | Carbo-hydrate (mg/ml) | Brix |
|---|---|---|---|---|---|---|
| MR Culture Filtrate | 16.1 | 0.37 | 13.1 | 0.78 | 5.5 | 4.0 |
| Blue Gel Col. Eluate | 6.2 | 0.10 | 232.6 | 8.0 | 0.35 | 2.8 |

B. Quantitative data on protein and enzyme

| | Total Applied | Passthrough | Retained & Eluted |
|---|---|---|---|
| Protein | 64.7 mg | ~22 mg | 30.3 mg |
| MR Activity | 1090 units[a] | 251 units | 849 units |

C. Application and recovery

| | |
|---|---|
| Protein Recovered | 47% of total applied |
| MR Activity Recovered | 78% of total applied[b] |

Note:
[a] 1 unit = (% strength) × (volume in ml)
[b] The remaining activity was in the pass-through fraction. In essence, there was no loss in activity in processing. The recovery (78%) is an indication of the capacity of the gel. If less protein were applied to the column, more than 85% of the enzyme could be recovered.

What is claimed is:

1. A method for the purification of a culture filtrate obtained by filtering the aqueous nutrient medium formed during the submerged fermentation of an organism of the species *Mucor miehei* therein which filtrate contains microbial rennet together with other proteins as impurities which method comprises:
   (a) contacting the culture filtrate with an affinity ligand of the formula:

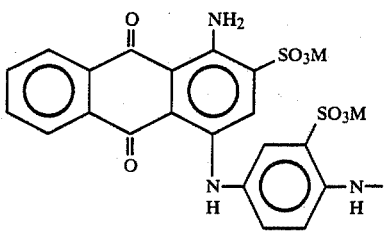

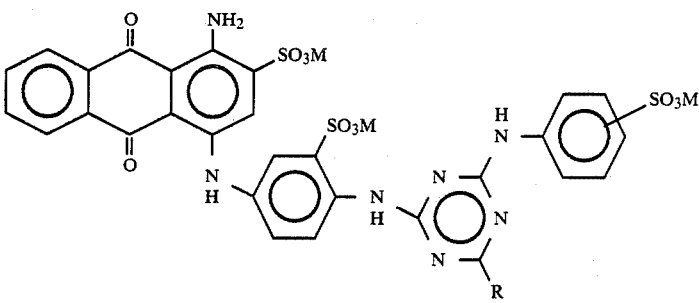

where M is a monovalent or divalent cation and R is a solubilizing moiety or a moiety which insolubilize the ligand without affecting its affinity characteristics, at a pH below 4.0 to cause the selective adsorption of the microbial rennet to the ligand thereby forming a ligand-/microbial rennet complex;
   (b) separating the ligand/microbial rennet complex from the other protein impurities; and
   (c) recovering the microbial rennet from the ligand microbial rennet complex.

2. The method of claim 1 wherein M is Na and R is Cl.

3. The method of claim 1 wherein R is polyethylene glycol, dextran or polyethyleneimine.

4. The method of claim 1 wherein M is Li+, Na+, K+, Rb+, Ca++ or Mg++.

5. A method for the purification of a culture filtrate obtained by filtering the aqueous nutrient formed during the submerged fermentation of an organism of the species *Mucor miehei* therein which filtrate contains microbial rennet together with other proteins as impurities which method comprises:
   (a) passing the culture filtrate downwardly through a column containing particles of an immobilized affinity ligand of the formula:

where M is a monovalent or divalent cation and R is agarose, polyacrylamide, an agarose-polyacrylamide copolymer, cellulose, glass or dextran cross-linked with epichlorhydrin, at a pH of below 4.0 causing the selective adsorption of the microbial rennet to the ligand thereby forming a ligand/microbial rennet complex;
   (b) eluting the microbial rennet from the ligand/rennet complex and
   (c) recovering the eluted microbial rennet in a purified form.

6. The method of claim 5 wherein R is agarose, polyacrylamide, an agarose-polyacrylamide copolymer, cellulose or glass.

7. The method of claim 5 wherein R is dextran cross-linked with epichlorhydrin.

8. The method of claim 5 wherein M is Na and R is cross-linked agarose.

9. The method of claim 5 wherein the bound rennet is eluted by contact with an eluting solution having a pH of 5 or above.

10. The method of claim 5 wherein elution is achieved by contacting the bound rennet with a salt solution.

* * * * *